US006548476B1

(12) United States Patent
Wu et al.

(10) Patent No.: US 6,548,476 B1
(45) Date of Patent: Apr. 15, 2003

(54) DIMERIC INHIBITORS OF INFLUENZA NEURAMINIDASE

(75) Inventors: Wen-Yang Wu, Victoria (AU); Betty Jin, Victoria (AU)

(73) Assignee: Biota Scientific Management Pty. Ltd., Victoria (AT)

( * ) Notice: Subject to any disclaimer, the term of this patent is extended or adjusted under 35 U.S.C. 154(b) by 3 days.

(21) Appl. No.: 09/658,445

(22) Filed: Sep. 8, 2000

Related U.S. Application Data

(63) Continuation of application No. PCT/AU00/00165, filed on Mar. 9, 2000.

(30) Foreign Application Priority Data

Mar. 12, 1999 (AU) .............................................. PP9139

(51) Int. Cl.$^7$ ...................... A61K 31/16; A61K 31/351; A61K 31/7012; C07D 309/28
(52) U.S. Cl. ................. 514/2; 435/5; 514/62; 530/322; 536/4.1; 536/55.1
(58) Field of Search .......................... 435/5; 514/2, 62, 514/459; 530/322, 395, 411; 536/4.1, 55.1; 549/415

(56) References Cited

U.S. PATENT DOCUMENTS

| 5,243,035 A | 9/1993 | Nakabayashi et al. ........ 536/4.1 |
| 5,759,823 A | 6/1998 | Wong et al. .................. 435/97 |

FOREIGN PATENT DOCUMENTS

| EP | 0 747 063 | 12/1996 |
| JP | 6038784 | 2/1994 |
| JP | 10182686 | 7/1998 |
| WO | 93/17033 | 9/1993 |
| WO | 94/06467 | 3/1994 |
| WO | 98/03524 | 7/1996 |
| WO | 96/26933 | 9/1996 |
| WO | 97/31006 | 8/1997 |
| WO | 97/32214 | 9/1997 |
| WO | 97/33896 | 9/1997 |
| WO | 98/03572 | 1/1998 |
| WO | 98/21243 | 5/1998 |
| WO | 98/46279 | 10/1998 |
| WO | 99/64037 | 12/1999 |

OTHER PUBLICATIONS

Meindl P. et al. "Inhibition of Neuraminidase Activity by Derivatives of 2–Deoxy–2,3–dehydro–N–acetylneuraminic Acid", Virology 58, pp. 457–463, 1974, Academic Press, Inc.

Meindl P. et al. "Synthese und Eigenschaften von 2–Deoxy–2,3–dehydroneuraminsaure sowie neuer N–Acyl–derivate", Monatshefte fur chemie 104, pp. 402–414, 1973, Springer–Verlag.

Kramer et al., "Spanning Binding Sites On Allosteric Proteins With Polymer–Linked Ligand Dimers", *Letters to Nature*, vol. 395:710–713, (1998).

*Primary Examiner*—Jeffrey E. Russel
(74) *Attorney, Agent, or Firm*—Foley & Lardner

(57) ABSTRACT

This invention relates to novel dimeric compounds, methods for their preparation, pharmaceutical formulations thereof, and their use as antiviral agents. The compounds are particularly useful against influenza virus. In particular the invention provides a dimeric compound which comprises two neuraminidase binding groups attached to a spacer or linking group. Preferably the dimeric molecule comprises two neuraminidase-binding neuraminic acid (sialic acid) or cyclopentyl or cyclohexenyl carboxylic acid derivatives covalently attached to a common spacer group. Pharmaceutical compositions and methods of treatment, prophylaxis and diagnosis are disclosed and claimed.

20 Claims, No Drawings

DIMERIC INHIBITORS OF INFLUENZA NEURAMINIDASE

This application is a Continuation-In-Part of PCT/AU00/00165, filed Mar. 9, 2000.

This invention relates to a new class of chemical compounds and their use in medicine. In particular the invention concerns novel dimeric compounds, methods for their preparation, pharmaceutical formulations thereof and their use as antiviral agents.

BACKGROUND OF THE INVENTION

Enzymes with the ability to cleave N-acetyl neuraminic acid (NANA), also known as sialic acid, from other carbohydrates are present in many microorganisms. These include bacteria such as *Vibrio cholerae, Clostridium perfringens, Streptococcus pneumoniae* and *Arthrobacter sialophilus*, and viruses such as influenza virus, parainfluenza virus, mumps virus, Newcastle disease virus and Sendai virus. Most of these viruses are of the orthomyxovirus or paramyxovirus groups, and carry a neuraminidase activity on the surface of the virus particles. Many of these neuraminidase-possessing organisms are major pathogens of man and/or animals, and some, such as influenza virus and Newcastle disease virus, cause diseases of enormous importance.

It has long been thought that inhibitors of neuraminidase might prevent infection by neuraminidase-bearing viruses. Most of the known neuraminidase inhibitors are analogues of neuraminic acid, such as 2-deoxy-2,3-dehydro-N-acetylneuraminic acid (DANA) and some of its derivatives (Meindl et al, Virology, 1974 58 457). Our International Patent Publication No. WO 91/16320 describes a number of analogues of DANA which are active against viral neuraminidase, and it has been shown in particular that 4-guanidino-2-deoxy-2,3-dehydro-N-acetylneuraminic acid (Compound (A), code number GG167) is useful in the treatment of influenza A and B (N. Engl. J. Med., 1997 337 874–880). Other patent applications describe various closely-related sialic acid derivatives (eg. PCT Publications No. WO 95/18800, No. WO 95/20583 and No. WO 98/06712), and anti-viral macromolecular conjugates of GG167 have also been described (International Patent Application No. PCT/AU97/00771).

Compound (A)

AC represents acetyl.

In addition to the sialic acid based inhibitors mentioned above, other types of highly active inhibitors of influenza virus neuraminidase have also been described, particularly those based on 5- and 6-membered carbocyclic ring systems (eg. International Patent Publications No. WO 96/26933 and No. 97/47194).

Recently, International Patent Publication No. WO 97/06157, No. WO 98/06712 and European Patent Application No. 0823428 have described certain derivatives of compound (A) in which the normal sialic acid 7-hydroxy group is replaced by various other functionalities, which inhibit multiplication of the influenza virus.

It will be clearly understood that, although a number of prior art publications are referred to herein, this reference does not constitute an admission that any of these documents forms part of the common general knowledge in the art, in Australia or in any other country.

We have now found that, surprisingly, when two neuraminidase-binding compounds are suitably linked together, through a region of the molecule that is not involved in binding to the active site, the resultant dimers show outstanding anti-viral activity. In particular we have found that, although an extra substituent attached to compound (A) at the 7-position generally causes a slight decrease in the anti-influenza activity, when two such 7-substituted molecules of compound (A) are both attached to a suitable spacer moiety, the anti-influenza activity can be greatly enhanced. The compounds have a longer duration of action than compound (A) alone. Though not wishing to be bound or limited by any proposed mechanism for the observed effect, we believe that the dimeric compounds of the invention have improved anti-influenza activity because they are able to bind to two separate neuraminidase molecules, and thereby cause aggregation of the neuraminidase tetramers and/or the influenza virions, or that by having one copy of zanamivir bound to the active site of the neuramindase, and a second copy in close proximity then the binding kinetics may be more efficient, in that as one copy dissociates the second copy can bind more rapidly than a free molecule of zanamivir. We have now shown that dimeric compounds have enhanced properties, including long duration of action. Again not wishing to be bound by theory, the basis for the long residence time in the lungs is thought to be due to the size and molecular weight of the macromolecule preventing entry through tight junctions in the respiratory epithelium, and the polarity of the macromolecule being such that passage through the cell membranes occurs very inefficiently. An alternative theory is that the compounds themselves interact with the phospholipids in the cell membrane or other components of the respiratory epithelium, and increase the residency time in the lungs.

SUMMARY OF THE INVENTION

In a first aspect the invention provides a dimeric compound which comprises two neuraminidase-binding groups attached to a spacer or linking group. The neuraminidase-binding group may be any compound which binds to the active site of influenza virus neuraminidase, provided that it is not cleaved by the enzyme. The neuraminidase binding group should itself have a high binding affinity; preferably the $IC_{50}$ or Kd for the neuraminidase binding group will be of $10^{-6}$ M or better. Preferably the dimeric compound comprises two neuraminidase-binding neuraminic acid (sialic acid) derivatives or cyclopentyl or cyclohexenyl carboxylic acid derivatives covalently attached to a common spacer group.

In a preferred embodiment, the invention provides a compound of General Formula I, and optical and geometric isomers thereof;

$$\text{(I)}$$

[Structure of formula (I): dimeric 2,3-dehydrosialic acid derivative connected via spacer Y at the 7-positions]

in which the neuraminidase binding group is a 2,3-dehydrosialic acid derivative which is attached to a spacer group Y via the 7-position;

R represents an azido group, a hydroxy group, an unsubstituted or substituted guanidino group, or an unsubstituted or substituted amino group;

$R^2$ represents $COCH_3$, $COCF_3$, $SO_2CH_3$ or $SO_2CF_3$;

X represents O, O(C=O), NH, NHCO, O(C=O)NH, O(C=S)NH, NH(C=O)NH, or NH(C=S)NH;

and the spacer group Y is an optionally substituted straight or branched or cyclic group or a combination thereof of up to 100 backbone atoms in length, with the backbone atoms selected from the group consisting of carbon, nitrogen, oxygen and sulphur;

or a pharmaceutically acceptable derivative thereof.

Preferably the spacer group Y is 8 to 100, more preferably 10 to 50, even more preferably 12 to 30 atoms long.

Preferably R is a substituted or unsubstituted amino or guanidino group, more preferably an amino or guanidino group.

Preferably $R^2$ is acetyl or trifluoroacetyl.

Preferably X is O or O(C=O)NH.

Most preferably:

R is an amino or guanidino group;

$R^2$ is acetyl or trifluoroacetyl;

X is O(C=O)NH; and

Y is a group of between 10 and 50 atoms in length.

The molecular weight of the compounds of the invention is generally in the range of from 650 to 500,000, preferably from 650 to 20,000, and even more preferably 650 to 2,000.

The biological activity of the compounds of the invention is based on the use of ligands on the backbone which are able to bind specifically to the active site of influenza virus neuraminidase, or of functionalised derivatives of such compounds. The term "neuraminidase binders" is used herein to refer to these compounds and their functionalized derivatives. The method and compounds of the invention can function either in the presence or the absence of compounds binding non-specifically to influenza virus neuraminidase. The neuraminidase binder may be any agent which binds to the active site of influenza virus neuraminidase, provided that it is not cleaved by the enzyme. The binding need not be irreversible, but the binding group should have a high binding affinity, preferably the $IC_{50}$ or the Kd will be of $10^{-6}$ M or less. The person skilled in the art will readily be able to optimize the spacer length by routine experimentation.

In general it is intended that when any variable occurs twice in formula (I), the variable may be the same or different.

Where R is an amino or guanidino group, suitable substituents include, but are not limited to, $C_{1-6}$alkyl, hydroxy$C_{1-6}$alkyl, allyl, nitrile, $C_{1-6}$alkoxycarbonyl and $C_{1-6}$acyl.

Suitable spacer groups Y include, but are not limited to, optionally substituted straight or branched hydrocarbon chains, peptides, oligosaccharides, poly amino acids, cyclodextrins, polyamidoamines, polyetheylenimines, polyalkyl and polyaryl ethers, polyamidoalcohols, polyethylene glycol units, alkylamidoalkanes, oligoacetates, oligolycolates, alkylureidoalkanes, EDTA, aryl, cycloalkyl, heterocyclic rings and heteroaryl groups, wherein the heteroatoms are selected from N, S, and O. Any one of these groups may be used alone, in multiple forms or in combination. The spacer group Y may also optionally have attached to it an extra functionality to improve the pharmaceutical or pharmacokinetic properties of the compound. Such functionalities include lipophilic hydrocarbon groups, polyethylene glycol (PEG) chains and peptides. Preferably the spacer group includes optionally substituted straight or branched hydrocarbon chains, polyaminoacids or EDTA.

For the purposes of this specification, the terms "hydrocarbon", "alkane" or "alkyl" are intended to include saturated, unsaturated and cyclic hydrocarbon groups, aromatic rings, and combinations of such groups. Suitable substituents on hydrocarbon chains include Br, Cl, F, I, $CF_3$, $NH_2$,substituted amino groups such as NHacyl, hydroxy, carboxy, $C_{1-6}$alkylamino and $C_{1-6}$alkoxy groups such as methoxy, and are preferably F, Cl, hydroxy, $C_{1-6}$alkoxy, amino, $C_{1-6}$alkylamino or $C_{1-6}$carboxy.

EDTA means ethylene dimeric tetraacetic acid.

It will be appreciated by those skilled in the art that the compounds of formula (I) may be modified to provide pharmaceutically acceptable derivatives thereof at any of the functional groups in the compounds of formula (I). Of particular interest as such derivatives are compounds modified at the carboxyl function, hydroxyl functions or at amino groups. Thus compounds of interest include $C_{1-6}$alkyl esters, such as methyl, ethyl, propyl or isopropyl esters, aryl esters, such as phenyl, benzoyl esters, and $C_{1-6}$acetyl esters of the compounds of formula (I).

It will be appreciated by those skilled in the art that the pharmaceutically acceptable derivatives of the compounds of formula (I) may be derivatised at more than one position.

The term "pharmaceutically acceptable derivative" means any pharmaceutically acceptable salt, ester or salt of such ester of a compound of formula (I) or any other compound which, upon administration to the recipient, is capable of providing a compound of formula (I) or an anti-virally active metabolite or residue thereof. Of particular interest as derivatives are compounds modified at the sialic acid carboxy or glycerol hydroxy groups, or at amino and guanidine groups.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic acid, while not in themselves pharmaceutically acceptable, may be useful in the preparation of salts useful as intermediates in obtaining compounds of the invention and their pharmaceutically acceptable acid addition salts.

Salts derived from appropriate bases include alkali metal (eg. sodium), alkaline earth metal (eg. magnesium), ammonium, and $NR_4^+$ (where R is $C_{1-4}$alkyl) salts.

The compounds of the invention may be prepared by the methods outlined below, in which Y, X, R and $R^2$ are as defined for formula (I).

Suitable monomeric intermediate compounds of general formula (II) can be prepared following methods described in International Patent Publications No. WO 97/06157 and No. WO 97/32214. Thus if the group at position 7 is an arylcarbonate (eg. Z=4-nitrophenoxy), the intermediate can be used to make 7-carbamate derivatives (Z=alkyl-NH) by reaction with various amines (alkyl-NH$_2$).

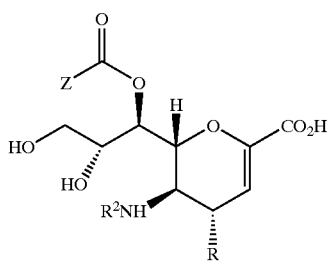

(II)

For example, the (6-aminohexyl)-7-carbamate derivative of GG167, compound (7) below, is a useful precursor to certain compounds of the invention.

Compound (7)

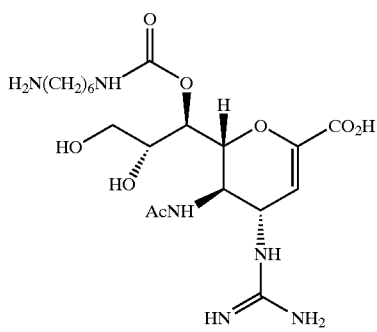

As will be appreciated by those skilled in the art, it may be necessary or desirable to use protecting groups to protect one or more of the functional groups of the neuraminidase-binding molecule during the process of attaching the monomers to the spacer group. See for example "Protective Groups in Organic Synthesis" by Theodore W. Greene and P. G. M. Wuts (John Wiley & Sons, 1991).

Conventional amino protecting groups may include for example aralkyl groups, such as benzyl, diphenylmethyl or triphenylmethyl groups; and acyl groups such as N-benzyloxycarbonyl or t-butoxycarbonyl.

Hydroxy groups may be protected, for example, by aralkyl groups, such as benzyl, diphenylmethyl or triphenylmethyl groups; acyl groups, such as acetyl; silicon protecting groups, such as trimethylsilyl groups; carbonate groups; acetals; or as tetrahydropyran derivatives.

Carboxylic acid groups are conveniently protected as the methyl or diphenylmethyl esters.

Removal of any protecting groups present may be achieved by conventional procedures.

Where it is desired to isolate a compound of the invention as a salt, for example as an acid addition salt, this may be achieved by treating the free base of general formula (I) with an appropriate acid, preferably with an equivalent amount, in a suitable solvent (e.g. aqueous ethanol).

Compounds of formula (I) may be prepared by coupling compounds of formula (III);

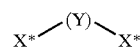

(III)

where X* is CO$_2$H, —COLG, NCO, -halide, —OH, —NHCOLG, —COLG, —OCSLG or —NHCSLG, where LG represents a leaving group such as halide or others obvious to those skilled in the art or protected derivatives thereof;

with compounds of formula (IV);

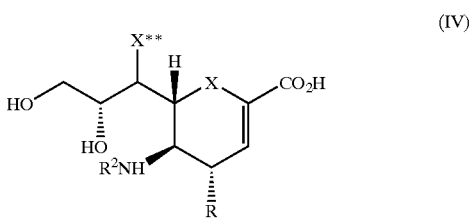

(IV)

where X** represents NH$_2$ or OH or activated or protected derivatives thereof, followed by de-protection if necessary.

The bond between X** and the glycerol side chain is either up or down according to the chemistry that is carried out; for example preparation of an ether leads to inversion of the stereochemistry at this point, but ultimately delivers material with the bond up (as shown in compounds of formula (I).

Preferably the leaving group is a halide.

The compounds of formula (I) possess antiviral activity. In particular these compounds are inhibitors of viral neuraminidase of orthomyxoviruses and paramyxoviruses, for example the viral neuraminidase of influenza A and B, parainfluenza, mumps and Newcastle disease.

Thus in a second aspect the invention provides a compound of the invention, preferably a compound of formula (I) or a pharmaceutically acceptable derivative thereof, for use as an active therapeutic agent in the treatment of orthomyxovirus and paramyxovirus infections.

In a third aspect the invention provides a method for the treatment of a viral infection, for example orthomyxovirus and paramyxovirus infections in a mammal, comprising the step of administration of an effective amount of a compound of the invention, preferably a compound of formula (I), or a pharmaceutically acceptable salt or derivative thereof, to a mammal in need of such treatment.

In a preferred embodiment of this aspect of the invention there is provided a method for the treatment of influenza A or B in a mammal, comprising the step of administration of an effective amount of a compound of the invention, preferably a compound of formula (I), or a pharmaceutically acceptable derivative thereof, to a mammal in need of such treatment.

Preferably the mammal is a human.

An alternative embodiment is a method for the treatment of a mammal suffering from a viral infection, for example, influenza, comprising the step of administration of an effective amount of a dimeric compound comprising two neuraminidase-binding groups attached to a spacer or linking group wherein the administration occurs once. Preferably the dimeric compound is a compound of formula (I) or a pharmaceutically acceptable derivative thereof.

In a fourth aspect the invention provides use of a compound of the invention for the manufacture of a medicament for the treatment of a viral infection.

It will be appreciated by those skilled in the art that reference herein to treatment extends to prophylaxis against infection as well as to the treatment of established infections or symptoms.

The compounds of the invention may also be used in diagnostic methods, in particular methods for the detection of influenza virus. For use in such methods it may be advantageous to link a compound of the invention to a label.

It will be further appreciated that the amount of a compound of the invention required for use in treatment will vary not only with the particular compound selected but also with the route of administration, the nature of the condition being treated, and the age and condition of the patient, and will ultimately be at the discretion of the attendant physician or veterinarian. In general however, a suitable dose will be in the range of from about 0.01 to 100 mg/kg of bodyweight per day, preferably in the range of 0.1 to 20 mg/kg/day.

For treatment, the compounds are effective when given post-infection; for example after the appearance of symptoms.

For prophylaxis, the compounds are effective when given before or at the time of exposure to infection.

Suitably treatment is given 1–2 times a fortnight, 1–2 times a week or 1–4 times daily and continued for 3–7 days post-infection, eg. 5 days, depending upon the particular compound used.

The desired dose may be presented in a single dose or as divided doses administered at appropriate intervals, for example as two, three, four or more sub-doses per day.

Preferably treatment is given once to twice a week, most preferably once a week. Preferably the compounds are administered for prophylactic purposes once or twice a week for the duration of one month.

The compound is conveniently administered in unit dosage form, for example containing 1 to 100 mg, conveniently 2 to 50 mg, most conveniently 5 to 20 mg of active ingredient per unit dosage form.

While it is possible that, for use in therapy, a compound of the invention may be administered as the raw chemical, it is preferable to present the active ingredient as a pharmaceutical formulation.

Thus in a fifth aspect the invention provides a pharmaceutical formulation comprising a compound of formula (I) or a pharmaceutically acceptable salt or derivative thereof, together with one or more pharmaceutically acceptable carriers therefor and, optionally, other therapeutic and/or prophylactic ingredients. The carrier(s) must be "acceptable" in the sense of being compatible with the other ingredients of the formulation and not being deleterious to the recipient thereof.

The compounds of the invention may also be used in combination with other therapeutic agents, for example other anti-infective agents. In particular the compounds of the invention may be employed with other antiviral agents. The invention thus provides in a sixth aspect a combination comprising a compound of formula (I) or a pharmaceutically acceptable salt or derivative thereof together with another therapeutically active agent, in particular an antiviral agent.

The combinations referred to above may conveniently be presented for use in the form of a pharmaceutical formulation, and thus such formulations comprising a combination as defined above together with a pharmaceutically acceptable carrier therefor comprise a further aspect of the invention.

Suitable therapeutic agents for use in such combinations include other anti-infective agents, in particular anti-bacterial and anti-viral agents such as those used to treat respiratory infections. For example, other compounds effective against influenza viruses, such as amantadine, rimantadine and ribavirin and the sialic acid analogues referred to above, may be included in such combinations.

The individual components of such combinations may be administered either sequentially or simultaneously in separate or combined pharmaceutical formulations.

When the compounds of the invention are used with a second therapeutic agent active against the same virus, the dose of each compound may either be the same as or different from that employed when each compound is used alone. Appropriate doses will be readily appreciated by those skilled in the art.

Pharmaceutical formulations include those suitable for oral, rectal, nasal, topical (including buccal and sub-lingual), vaginal or parenteral (including intramuscular, subcutaneous and intravenous) administration, or those in a form suitable for administration to the respiratory tract (including the nasal passages) for example by inhalation or insufflation. The formulations may, where appropriate, be conveniently presented in discrete dosage units, and may be prepared by any of the methods well known in the art of pharmacy. These methods include the step of bringing into association the active compound with liquid carriers or finely divided solid carriers or both, and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may for example be in the form of aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles, which may include edible oils, or preservatives.

The compounds according to the invention may also be formulated for parenteral administration by injection, for example bolus injection, or continuous infusion, and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulating agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Formulations suitable for topical administration in the mouth include lozenges comprising active ingredient in a flavoured base, usually sucrose and gum acacia or gum tragacanth; pastilles comprising the active ingredient in an inert base such as gelatin or sucrose and gum acacia; and mouthwashes comprising the active ingredient in a suitable liquid carrier.

For administration to the respiratory tract, including intra-nasal administration, the neuraminidase inhibitors may be administered by any of the methods and formulations employed in the art for administration to the respiratory tract.

Thus in general for administration to the respiratory tract the compounds may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethlene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds may be provided in the form of a dry powder, or a dry powder mixture, for example a powder mix of the compound in a suitable powder base such as lactose, starch, starch derivatives such as hydroxypropylmethyl cellulose and polyvinylpyrrolidine (PVP). The powder composition may be presented in unit dose form, for example in capsules or cartridges of eg. gelatin, or blister packs from which the powder may be administered by means of an inhaler.

In formulations intended for administration to the respiratory tract, including intranasal formulations, the compound will generally have a small particle size, for example of the order of 10 microns or less (Mass median aerodynamic diameter). Such a particle size may be obtained by means known in the art, for example by micronisation.

Preferably the compounds of the invention are administered to the respiratory tract by inhalation, insufflation, or intranasal administration.

When desired, formulations adapted to give sustained release of the active ingredient may be employed.

For the purposes of this specification it will be clearly understood that the word "comprising" means "including but not limited to", and that the word "comprises" has a corresponding meaning.

DETAILED DESCRIPTION OF THE INVENTION

The invention will now be described in detail by way of reference only to the following non-limiting examples.

Particular examples of compounds of the invention include those of Formula (Ia), in which the spacer group Y is as shown in Table 1 below.

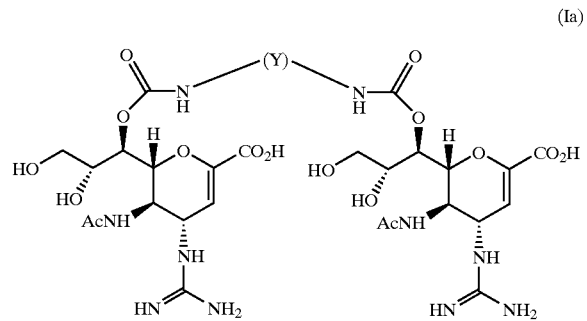

(Ia)

TABLE 1

| Compound Number | Linking Group Y |
|---|---|
| (2) | $(CH_2)_6NHCONH(CH_2)_4NHCONH(CH_2)_6$ |
| (3) | $(CH_2)_6NHCONH(CH_2)_{12}NHCONH(CH_2)_6$ |
| (4) | $(CH_2)_6NH[COCH_2NH]_3CONH(CH_2)_6NHCO[NHCH_2CO]_3NH(CH_2)_6$ |
| (5) | $(CH_2)_6NH[CO(CH_2)_5NH]_2CONH(CH_2)_{12}NHCO[NH(CH_2)_5CO]_2NH(CH_2)_6$ |
| (6) | $(CH_2)_6NH[CO(CH_2)_5NH]_4CONH(CH_2)_6NHCO[NH(CH_2)_5CO]_4NH(CH_2)_6$ |
| (8) | $(CH_2)_6NHCOCH_2N[CH_2CO_2H]CH_2CH_2N[CH_2CO_2H]CH_2CONH(CH_2)_6$ |
| (9) | $(CH_2)_6NHCO(CH_2)_2CH[NH_2 \cdot TFA]CONHCH_2CONH(CH_2)_6$ |
| (10) | $CH_2CH_2OCH_2CH_2OCH_2CH_2$ |

EXAMPLE 1

Preparation of Bis-[7-(6'-ethylene-ureidohexyl)-carbamoyloxy-5-acetamido-4-guanidino-2,3,4,5-tetradeoxy-D-glycero-D-galacto-non-2-enopyranosonic acid] (2)

To a solution of 5-acetamido-7-(6'-aminohexyl)-carbamoyloxy-4-guanidino-2,3,4,5-tetradeoxy-D-glycero-D-galacto-non-2-enopyranosonic acid (7) (50 mg, 0.1055 mmole) in a mixture of DMSO (1 ml) and pyridine (2.5 ml) were added 1,4-diisocyanatobutane (7.39 mg, 0.0527 mmole) and 4-dimethylaminopyridine (12.87 mg, 0.1055 mmole). The whole mixture was stirred under argon at 50° C. for 7 days. The mixture was filtered and the filtrate was evaporated under high vacuum to dryness. The residue was stirred in acetone (2×20 ml) at room temperature for 24 hr and filtered. The filter-cake was washed with acetone (5 ml) and recrystallized from a mixture of methanol and water (7:3) to afford the title compound (2) as a white solid (18.6 mg, 32%).

MS 1090 (M+2)++

$^{1}$H-nmr (CD$_{3}$OD+D$_{2}$O) δ (ppm): 1.30–1.70 (m, 20H), 2.01 (br s, 6H), 2.95–3.20 (m, 12H), 3.50–3.65 (m, 2H), 3.70–3.80 (m, 2H), 3.90–4.20 (m, 4H), 4.35–4.70 (m, 6H), 5.70 (br, 2H).

EXAMPLE 2

Preparation of Bis-[7-(6'-hexyleneureodo)-carbamoyloxy-5-acetamido-4-guanidino-2,3,4,5-tetradeoxy-D-glycero-D-galacto-non-2-enopyranosonic acid] (3)

To a solution of 5-acetamido-7-(6'-aminohexyl)-carbamoyloxy-4-guanidino-2,3,4,5-tetradeoxy-D-glycero-D-galacto-non-2-enopyranosonic acid (7) (50 mg, 0.1055 mmole) in a mixture of DMSO (1 ml) and pyridine (2.5 ml) were added 4-dimethylaminopyridine (12.87 mg, 0.1055 mmole) and 1,12-diisocyanatododecane (13.31 mg, 0.0527 mmole). The whole mixture was stirred under argon at 50° C. for 7 days and then filtered. The filtrate was evaporated under high vacuum to dryness. The residue was taken up in acetone (2×30 ml), redissolved in DMSO (1 ml), then diluted with a mixture of acetone and ether (1:1) (100 ml) to afford a white precipitate. After filtration, the filter cake was washed with acetone (20 ml) and air-dried to give a crude product (3), which was then recrystallized from a mixture of methanol and water to afford the title compound (3) as a white powder (15 mg, 23.6%).

MS 1202 (M+2)++

$^{1}$H-nmr (CD$_{3}$OD+D$_{2}$O) δ (ppm): 1.25–1.70 (m, 36H), 1.98 (br, s, 6H), 2.95–3.20 (m, 12H), 3.35–3.70 (m, 4H), 3.80–4.60 (m, 10H), 5.65 (br, 2H).

EXAMPLE 3

Preparation of amino acid-linked Bis-[GG167-7-carbamate]; Compounds No. (4), (5) and (6)

In a similar manner to that described in Examples 1 and 2, compounds (4), (5) and (6) were each prepared using the 6-aminohexyl-7-carbamate compound (7), or protected forms of (7), as the key starting material. Each compound was characterised by its mass spectrum and Nmr data.

EXAMPLE 4

Preparation of Bis-[7-(6'-methyleneamine-N-acetic acid-N-acetamido-hexyl)-carbamoyloxy-5-acetamido-4-guanidino-2,3,4,5-tetradeoxy-D-glycero-D-galacto-non-2-enopyranosonic acid] (Compound Number (8))

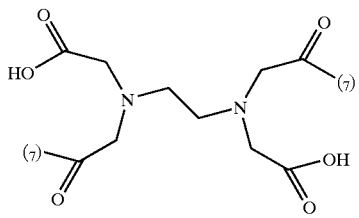

To a solution of 5-acetamido-7-(6'-aminohexyl)-carbamoyloxy-4-guanidino-2,3,4,5-tetradeoxy-D-glycero-D-galacto-non-2-enopyranosonic acid (7) (76 mg, 0.16 mmole) in a mixture of DMF (7.5 ml) and pyridine (2.5 ml) were added ethylenediaminetetraacetic dianhydride (20.5 mg, 0.08 mmole) and 4-(dimethylamino)pyridine (3.5 mg, 0.028 mmole). The whole mixture was stirred at 50° C. for 18 hr, then evaporated to dryness under high vacuum. The residue was partitioned between dichloromethane (20 ml) and water (10 ml). The aqueous solution was washed with dichloromethane (10 ml), ethyl acetate (10 ml), then evapotated to dryness under high vacuum. The residue was triturated in acetone (50 ml×2) and filtered. The solid was dissolved in water (0.5 ml) and chromatographed on a Sephadex G-25 (50 ml) column using water as eluent and the product was freeze-dried, to afford the title compound (8) (30 mg, 31%).

MS 1206 ( M+2)

$^{1}$H-nmr (D$_{2}$O) δ (ppm): 1.23–1.63 (m, 16H), 1.98 (brs, 6H), 3.00–3.20 (m, 8H), 3.35–3.55 (m, 6H), 3.60–3.92 (m, 10H), 4.08 (m, 4H), 4.43 (dd, 2H), 4.50 (dd, 2H), 4.84 (dd, 2H), 5.66 (br, 2H).

EXAMPLE 5

Preparation of D-glutam-γ-yl-α-ylamineacetyl, di-[7-(6'-aminohexyl)-carbamoyloxy-5-acetamido-4-guanidino-2,3,4,5-tetradeoxy-D-glycero-D-galacto-non-2-enopyranosonic acid] as trifluoroacetic acid salt (Compound Number (9))

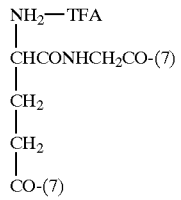

N-Boc-D-glutam-α-ylamineacetic acid (25 mg, 0.082 mmole) was dissolved in water (0.25 ml) containing triethylamine (16.6 mg, 0.164 mmole) and N-methylmorpholine (16.6 mg, 0.164 mmole). The clear solution was diluted with acetone (3 ml), then cooled to −20° C. in a dry ice-acetone bath. Into this solution was added isobutyl chloroformate (26.95 mg, 0.197 mmole). The reaction mixture was stirred at −15°±2° C. for 12 min., then combined with a solution of 5-acetamido-7-(6'-aminohexyl)carbamoyloxy-4-guanidino-2,3,4,5-tetradeoxy-D-glycero-D-galacto-non-2-enopyranosonic acid (7) (116.9 mg, 0.246 mmole) and triethylamine (24.9 mg, 0.246 mmole) in water (2.5 ml). The resulting mixture was allowed to agitate at room temperature for 3 hr, then evaporated to dryness under reduced pressure. The residue was subjected to flash column-chromatography (silica gel, 2-propanol:acetic acid:water=3:1:1 as eluent) to afford the N-Boc derivative of the title compound (9), which was then treated with trifluoroacetic acid (2 ml) at room temperature for 1 hr, evaporated under vacuum to dryness. The residue was freeze-dried to give the title compound (9) as trifluoroacetic acid salt (31 mg, 30.4%)

MS 1118 (M+2)

$^{1}$H-nmr (D$_{2}$O) δ (ppm): 1.22–1.62 (m, 16H), 1.98 (br., 6H), 2.20 (m, 2H), 2.41 (m, 1H), 2.57 (m, 1H), 2.90–3.25 (m, 8H), 3.59 (br dd, 2H), 3.68 (br dd, 2H), 3.76–4.01 (m, 3H), 4.10 (m, 4H), 4.43 (br dd, 2H), 4.53 (br dd, 2H), 4.95 (br dd, 2H), 5.85 (br., 2H)

EXAMPLE 6

Inhibition of Influenza Virus Replication by Compounds of the Invention

Compounds of the invention were tested for their ability to inhibit the replication of influenza A virus, essentially following the standard method that has been described in the literature (see for example Watanabe et al, J. Virological Methods, 1994 48 257). The assay was carried out using MDCK cells, and the results are shown in Table 2 below. The results are shown as $ID_{50}$, the minimum compound concentration that inhibits cytopathic effect by 50% [(μg/ml)], calculated by using a regression analysis program for semi-log curve fitting. The results show that dimeric compounds (2), (3) and (4) are all more active against influenza than the monomeric ligand molecule (7), and that compound (2) of the invention is even more potent than the highly active compound (A) [GG167]. The therapeutic index for the compounds can be calculated by dividing the minimum cytotoxic drug concentration (MTC) by the $ID_{50}$.

TABLE 2

| Compound No. | Spacer Atoms (Number of Atoms) | $ID_{50}$ μg/ml | $ID_{50}$ (μg of (A)) | MTC μg/ml |
|---|---|---|---|---|
| (2) | 22 | 0.007 | 0.013 | >10 |
| (3) | 30 | 0.017 | 0.028 | >10 |
| (4) | 42 | 0.084 | 0.11 | >10 |
| (5) | 58 | 0.35 | 0.42 | >10 |
| (6) | 78 | 0.63 | 0.62 | >10 |
| (A) | — | 0.0095 | 0.028 | >10 |
| (7) | — | 0.22 | 0.32 | >10 |

EXAMPLE 7

Inhibition of Influenza Virus Replication by Compounds of the Invention

Compounds of the invention were tested for their ability to inhibit the replication of influenza A/Victoria/3/75 B010 in a standard CPE type assay similar to that described above in Example 6. The results for three separate experiments are shown in Table 3 below.

TABLE 3

| Compound No. | $EC_{50}$ (μg/ml) | $EC_{90}$ (μg/ml) | $CC_{50}$ (μg/ml) |
|---|---|---|---|
| 8 (test 1) | 0.00971 | 0.0671 | >0.1 |
| 9 (test 2) | 0.002 | — | >1 |
| 9 (test 3) | 0.0004 | — | >0.1 |
| Compound (A) (test 2) | 0.009 | — | >1 |
| Compound (A) (test 3) | 0.009 | — | >0.1 |

EXAMPLE 8

Assessment of Long Duration of Action

Rodents are anaesthetised and dosed with compound of interest by the intra-tracheal route at a dose volume of 0.8 ml/kg. The rodent is then held in the vertical position until full recovery is achieved. At different time points, for example, 2, 8, 24 and 48 hours post-dose, levels of compound in the lung tissue are assessed by analytical methods. The time at which levels of compound fall below the sensitivity of the analytical techniques identified will determine the residency time of the compound in lung tissue.

EXAMPLE 9

Alternative Assessment of Long Duration of Action and Efficacy

The protocol for infecting mice has been described previously (1, 2 ,3, 4). Mildly anaesthetised mice are inoculated into the external nares with influenza virus.

Treatment procedure and regimen. A single dose of compound is administered at a defined time point up to 10 days prior to infection, preferably 4–7 days prior to infection, or following infection, preferably immediately following infection and up to 48 hours post infection. In most experiments, a non-lethal strain of influenza is used, and efficacy is assessed by reductions in lung virus titre. For mice given compound prior to infection, lungs are removed post infection either on a single day, or on days following infection, preferably days 1–4 post infection. Homogenised lung samples are assayed for virus using established methods, and the titres of viral load estimated and compared to titres of virus in lungs of untreated mice.

In those experiments where a mouse-adapted lethal strain of influenza is used, efficacy is assessed by an increase in survival rate and/or numbers of survivors, as compared to untreated mice.

Ryan, D. M., J. Ticehurst, M. H. Dempsey, and C. R. Penn, 1994. Inhibition of influenza virus replication in mice by GG167 (4-guanidino-2,4-dideoxy-2,3-dehydro-N-acetylneuraminic acid) is consistent with extracellular activity of viral neuraminidase (sialidase). Antimicrob. Agents and Chemother. 38 (10):2270–2275.

von Itzstein M., W.-Y. Wu, G. B. Kok, M. S. Pegg, J. C. Dyason, B. Jin, T. V. Phan, M. L. Smythe, H. F. White, S. W. Oliver, P. M. Colman, J. N. Varghese, D. M. Ryan, J. M. Woods, R. C. Bethell, V. J. Hotham, J. M. Cameron, and C. R. Penn. 1993. Rational design of potent sialidase-based inhibitors of influenza virus replication. Nature (London) 363: 418–423

Woods, J. M. R. C. Bethell, J. A. V. Coates, N. Healey, S. A. Hiscox, B. A. Pearson, D. M. Ryan, J. Ticehurst, J. Tilling, S, A. Walcott, and C. R. Penn. 1993. 4-Guanidino-2,4-dideoxy-2,3-dehydro-N-acetylneuraminic acid is a highly effective inhibitor both of the sialidase (neuraminidase) and of growth of a wide range of influenza A and B viruses in vitro. Antimicrob. Agents Chemother. 37: 1473–1479

Robert J Fenton, Peter J Morley, Ian J Owens, David Gower, Simon Parry, Lee Crossman And Tony Wong (1999). Chemoprophylaxis of influenza A virus infections, with single doses of zanamivir, demonstrates that zanamivir is cleared slowly from the respiratory tract. Antimicrob. Agents and Chemother. 43, 11, 2642–2647

EXAMPLE 10

Powder Inhalation Formulation

Active Ingredient. 5 mg

Carrier e.g. lactose 20 mg

The active ingredient and the carrier are mixed together in a tumbling mixer.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A compound of General Formula I:

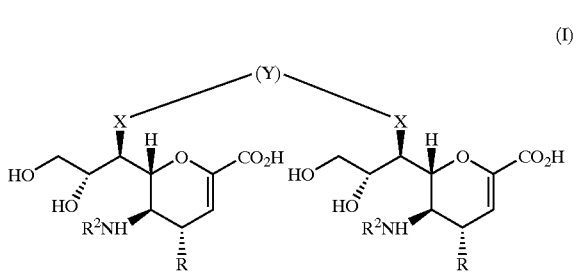

wherein

R represents an azido group, a hydroxy group, an unsubstituted or substituted guanidino group, or an unsubstituted or substituted amino group;

$R^2$ represents $COCH_3, COCF_3, SO_2CH_3$ or $SO_2CF_3$;

X represents O, O(C=O), NH, NHCO, O(C=O)NH, O(C=S)NH, NH(C=O)NH, or NH(C=S)NH;

and the spacer group Y is an optionally substituted straight, or branched or cyclic group or combination thereof, of up to 100 atoms in length, with the backbone atoms selected from the group consisting of carbon, nitrogen, oxygen and sulphur;

or a pharmaceutically-acceptable derivative thereof.

2. A compound according to claim 1, wherein Y is a spacer group that is 8 to 100 atoms long.

3. A compound according to claim 2, wherein Y is 10 to 50 atoms long.

4. A compound according to claim 3, wherein Y is 12 to 30 atoms long.

5. A compound according to claim 1, in which:

R is an amino or guanidino group, which may optionally be substituted;

$R^2$ is acetyl or trifluoroacetyl;

X is O(C=O)NH; and

Y is a group of between 10 and 50 atoms in length.

6. A compound according to claim 5, in which the substituent on the R group is selected from the group consisting of $C_{1-6}$alkyl, hydroxy$C_{1-6}$alkyl, allyl, nitrile, $C_{1-6}$alkoxycarbonyl and $C_{1-6}$acyl.

7. A compound according to claim 1, wherein Y is selected from the group consisting of optionally substituted straight or branched hydrocarbon chains, peptides, oligosaccharides, poly amino acids, cyclodextrins, polyamidoamines, polyetheylenimines, polyalkyl and polyaryl ethers, polyamidoalcohols, polyethylene glycol units, alkylamidoalkanes, oligoacetates, oligolycolates, alkylureidoalkanes, EDTA, aryl, cycloalkyl, heterocyclic rings and heteroaryl groups, wherein the heteroatoms are selected from N, S, and O, any of which groups may be used alone, in multiple forms or in combination.

8. A compound according to claim 1, in which the compound is of formula (Ia)

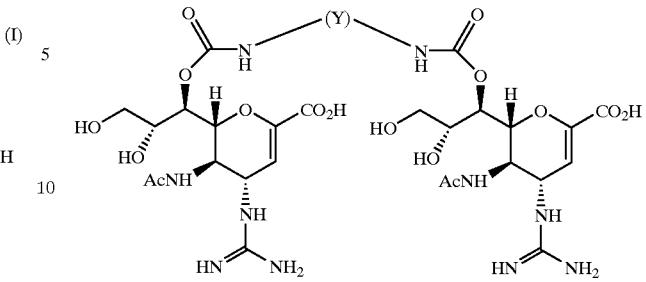

and Y is $(CH_2)_6NHCONH(CH_2)_4NHCONH(CH_2)_6$, $(CH_2)_6NHCONH(CH_2)_{12}NHCONH(CH_2)_6$, $(CH_2)_6NH[COCH_2NH]_3CONH(CH_2)_6NHCO[NHCH_2CO]_3NH(CH_2)_6$, $(CH_2)_6NH[CO(CH_2)_5NH]_2CONH(CH_2)_{12}NHCO[NH(CH_2)_5CO]_2NH(CH_2)_6$, $(CH_2)_6NH[CO(CH_2)_5NH]_4CONH(CH_2)_6NHCO[NH(CH_2)_5CO]_4NH(CH_2)_6$, $(CH_2)_6NHCOCH_2N[CH_2CO_2H]CH_2CH_2N[CH_2CO_2H]CH_2CONH(CH_2)_6$, $(CH_2)_6NHCO(CH_2)_2CH[NH_2.TFA]CONHCH_2CONH(CH_2)_6$, or $CH_2CH_2OCH_2CH_2OCH_2CH_2$.

9. A compound according to claim 1, wherein Y has attached to it an extra functionality to improve the pharmaceutical or pharmacokinetic properties of the compound, selected from the group consisting of lipophilic hydrocarbon groups, polyethylene glycol (PEG) chains and peptides.

10. A pharmaceutical composition comprising a compound according claim 1, together with a pharmaceutically acceptable carrier and, optionally, one or more other therapeutic and/or prophylactic ingredients.

11. A composition according to claim 10, additionally comprising a second anti-viral agent.

12. A composition according to claim 11, in which the second anti-viral agent is selected from the group consisting of sialic acid analogues, amantadine, rimantadine and ribavirin.

13. A method for the treatment or prophylaxis of an orthomyxovirus or paramyxovirus infection in a mammal, comprising the step of administration of an effective amount of a compound according to claim 1 to a mammal in need of such treatment.

14. A method according to claim 13, in which the infection is caused by influenza A or B.

15. A method according to claim 13, in which the mammal is a human.

16. A method according to claim 13, in which the compound is of Formula (I)

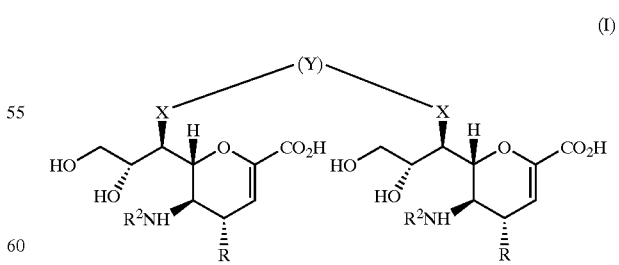

wherein

R is an amino guanidino group, which may optionally be substituted;

$R^2$ is acetyl or trifluoroacetyl;

X is O(C=O)NH; and

Y is a group of between 10 and 50 atoms in length;
or Formula (Ia)

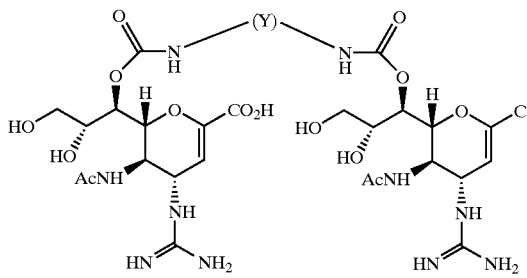

(Ia)

wherein Y is $(CH_2)_6NHCONH(CH_2)_4NHCONH(CH_2)_6$, $(CH_2)_6NHCONH(CH_2)_{12}NHCONH(CH_2)_6$, $(CH_2)_6NH[COCH_2NH]_3CONH(CH_2)_6NHCO[NHCH_2CO]_3NH(CH_2)_6$, $(CH_2)_6NH[CO(CH_2)_5NH]_2CONH(CH_2)_{12}NHCO[NH(CH_2)_5CO]_2NH(CH_2)_6$, $(CH_2)_6NH[CO(CH_2)_5NH]_4CONH(CH_2)_6NHCO[NH(CH_2)_5CO]_4NH(CH_2)_6$, $(CH_2)_6NHCOCH_2N[CH_2CO_2H]CH_2CH_2N[CH_2CO_2H]CH_2CONH(CH_2)_6$, $(CH_2)_6NHCO(CH_2)_2CH[NH_2.TFA]CONHCH_2CONH(CH_2)_6$, or $CH_2CH_2OCH_2CH_2OCH_2CH_2$.

17. A method according to claim 13, in which the compound is administered at a dose of from about 0.01 to 100 mg/kg of bodyweight per day.

18. A method for the detection of influenza virus, comprising the step of contacting a compound according to claim 1 with a sample suspected of comprising the virus.

19. A method for the treatment of a mammal suffering from a viral infection, comprising the step of administration of an effective amount of a compound of General Formula (I):

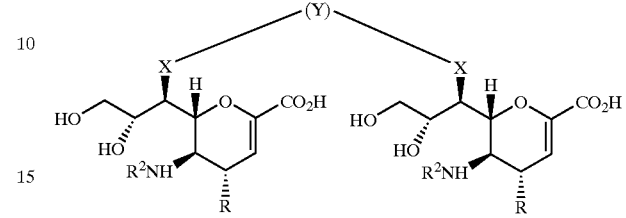

or a pharmaceutically acceptable derivative thereof, wherein:
  R is an amino or guanidino group, which may optionally be substituted;
  $R^2$ is acetyl or trifluoroacetyl;
  X is $O(C=O)NH$; and
  Y is a group of between 10 and 50 atoms in length;
  wherein said administration occurs once.

20. A method according to claim 19, in which the viral infection is influenza.

* * * * *